United States Patent
Seibel et al.

(10) Patent No.: US 9,561,078 B2
(45) Date of Patent: Feb. 7, 2017

(54) MULTI-CLADDING OPTICAL FIBER SCANNER

(75) Inventors: Eric Seibel, Seattle, WA (US); Richard Johnston, Sammamish, WA (US); Charles David Melville, Issaquah, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 2564 days.

(21) Appl. No.: 12/281,251

(22) PCT Filed: Mar. 3, 2006

(86) PCT No.: PCT/US2006/007704
§ 371 (c)(1),
(2), (4) Date: Aug. 29, 2008

(87) PCT Pub. No.: WO2007/106075
PCT Pub. Date: Sep. 20, 2007

(65) Prior Publication Data
US 2009/0024191 A1    Jan. 22, 2009

(51) Int. Cl.
*A61N 5/06* (2006.01)
*A61B 18/22* (2006.01)
(Continued)

(52) U.S. Cl.
CPC .............. *A61B 18/22* (2013.01); *A61B 1/0008* (2013.01); *A61B 1/0017* (2013.01);
(Continued)

(58) Field of Classification Search
USPC .... 607/92; 385/115–119, 126–128; 356/73.1
See application file for complete search history.

(56) References Cited

U.S. PATENT DOCUMENTS 4,118,270 A    10/1978  Pan et al. ...................... 156/659
4,234,788 A    11/1980  Palmer et al. ................. 250/227
(Continued)

FOREIGN PATENT DOCUMENTS

DE    4428967    12/1995    ............ A61B 17/36
EP    0 713 672   5/1996    ............... A61B 1/00
(Continued)

OTHER PUBLICATIONS

Barhoum et al., "Optical modeling of an ultrathin scanning fiber endoscope, a preliminary study of confocal versus non-confocal detection." *Optics Express*, vol. 13, No. 19: 7548-7562, Sep. 19, 2005.
(Continued)

*Primary Examiner* — Nicholas Lucchesi
*Assistant Examiner* — Matthew Saunders
(74) *Attorney, Agent, or Firm* — Blakely Sokoloff Taylor & Zafman LLP (57) ABSTRACT

A multi-cladding optical fiber includes a core that conveys visible light used by a scanner for imaging a site within a patient's body, and an inner cladding that conveys high-power light, such as infrared light, used for providing therapy to site. The distal end of multi-cladding optical fiber is driven to scan the site when imaging or rendering therapy using an actuator. High-power light is coupled into inner cladding at proximal end of optical fiber using several different techniques. Some techniques use an axicon to direct the high-power light into the inner cladding, while visible light is coupled directly into the core. Another technique uses a multimode optical fiber in a coupling relationship with the multi-cladding optical fiber, to transfer high-power light from a core of the multimode fiber into the inner cladding of the multi-cladding optical fiber.

15 Claims, 7 Drawing Sheets

(51) Int. Cl.
*A61B 1/00* (2006.01)
*A61B 1/07* (2006.01)
(52) U.S. Cl.
CPC ............ *A61B 1/00172* (2013.01); *A61B 1/07* (2013.01); *A61B 2018/2238* (2013.01); *A61B 2090/373* (2016.02)

(56) References Cited

U.S. PATENT DOCUMENTS

| | | | | |
|---|---|---|---|---|
| 4,265,699 | A | 5/1981 | Ladany | 156/657 |
| 4,410,235 | A | 10/1983 | Klement et al. | 350/96.18 |
| 4,454,547 | A | 6/1984 | Yip et al. | 358/293 |
| 4,626,652 | A * | 12/1986 | Bjork et al. | 219/121.68 |
| 4,686,963 | A | 8/1987 | Cohen et al. | 128/4 |
| 4,688,555 | A | 8/1987 | Wardle | 128/4 |
| 4,695,163 | A | 9/1987 | Schachar | 356/369 |
| 4,710,619 | A | 12/1987 | Haberl | 250/203 |
| 4,743,283 | A | 5/1988 | Borsuk | 65/2 |
| 4,750,795 | A * | 6/1988 | Blotekjaer | 385/24 |
| 4,758,222 | A | 7/1988 | McCoy | 604/95 |
| 4,762,118 | A | 8/1988 | Lia et al. | 128/4 |
| 4,768,513 | A | 9/1988 | Suzuki | 128/634 |
| 4,782,228 | A | 11/1988 | Westell | 250/236 |
| 4,804,395 | A | 2/1989 | Clark et al. | 65/2 |
| 4,815,079 | A * | 3/1989 | Snitzer et al. | 372/6 |
| 4,824,195 | A | 4/1989 | Khoe | 350/96.18 |
| 4,850,364 | A | 7/1989 | Leavitt | 128/661.09 |
| 4,928,316 | A | 5/1990 | Heritage et al. | 455/600 |
| 4,979,496 | A | 12/1990 | Komi | 128/4 |
| 4,983,165 | A | 1/1991 | Loiterman | 604/95 |
| 5,037,174 | A | 8/1991 | Thompson | 385/33 |
| 5,074,642 | A | 12/1991 | Hicks | 385/116 |
| 5,103,497 | A | 4/1992 | Hicks | 385/117 |
| 5,172,685 | A | 12/1992 | Nudelman | 128/6 |
| 5,187,759 | A * | 2/1993 | DiGiovanni et al. | 385/27 |
| 5,199,431 | A * | 4/1993 | Kittrell et al. | 600/477 |
| 5,209,117 | A | 5/1993 | Bennett | 73/517 |
| 5,231,286 | A | 7/1993 | Kajimura et al. | 250/234 |
| 5,247,174 | A | 9/1993 | Berman | 250/235 |
| 5,272,330 | A | 12/1993 | Betzig et al. | 250/216 |
| 5,286,970 | A | 2/1994 | Betzig et al. | 250/227.26 |
| 5,305,759 | A | 4/1994 | Kaneko et al. | 600/476 |
| 5,321,501 | A | 6/1994 | Swanson et al. | 356/345 |
| 5,360,968 | A | 11/1994 | Scott | 235/454 |
| 5,381,782 | A | 1/1995 | DeLaRama et al. | 128/4 |
| 5,394,500 | A | 2/1995 | Marchman | 385/123 |
| 5,405,337 | A | 4/1995 | Maynard | 604/281 |
| 5,425,123 | A | 6/1995 | Hicks | 385/117 |
| 5,459,803 | A | 10/1995 | Yamane et al. | 385/33 |
| 5,480,046 | A | 1/1996 | Filas et al. | 216/7 |
| 5,507,725 | A | 4/1996 | Savage et al. | 604/95 |
| 5,512,035 | A | 4/1996 | Konstorum et al. | 600/146 |
| 5,535,759 | A | 7/1996 | Wilk | 128/898 |
| 5,549,542 | A | 8/1996 | Kovalcheck | 600/146 |
| 5,563,969 | A | 10/1996 | Honmou | 385/35 |
| 5,570,441 | A | 10/1996 | Filas et al. | 385/43 |
| 5,627,922 | A | 5/1997 | Kopelman et al. | 385/12 |
| 5,643,175 | A | 7/1997 | Adair | 600/133 |
| 5,649,897 | A | 7/1997 | Nakamura et al. | 600/111 |
| 5,668,644 | A | 9/1997 | Kuroiwa et al. | 358/480 |
| 5,703,979 | A | 12/1997 | Filas et al. | 385/43 |
| 5,715,337 | A | 2/1998 | Spitzer et al. | 385/4 |
| 5,724,169 | A | 3/1998 | LaGasse | 359/173 |
| 5,727,098 | A | 3/1998 | Jacobson | 385/31 |
| 5,765,561 | A | 6/1998 | Chen et al. | 128/653.1 |
| 5,894,122 | A | 4/1999 | Tomita | 250/234 |
| 5,906,620 | A | 5/1999 | Nakao et al. | 606/113 |
| 5,919,200 | A | 7/1999 | Stambaugh et al. | 606/159 |
| 5,926,592 | A * | 7/1999 | Harris et al. | 385/33 |
| 5,933,437 | A * | 8/1999 | Delavaux | 372/6 |
| 5,939,709 | A | 8/1999 | Ghislain et al. | 250/216 |
| 5,947,905 | A | 9/1999 | Hadjicostis et al. | 600/463 |
| 5,984,860 | A | 11/1999 | Shan | 600/116 |
| 5,991,697 | A | 11/1999 | Nelson et al. | 702/49 |
| 6,035,229 | A | 3/2000 | Silverstein et al. | 600/473 |
| 6,038,363 | A * | 3/2000 | Slater et al. | 385/147 |
| 6,046,720 | A | 4/2000 | Melville et al. | 345/108 |
| 6,069,698 | A | 5/2000 | Ozawa et al. | 356/345 |
| 6,081,605 | A | 6/2000 | Roth et al. | 382/103 |
| 6,091,067 | A | 7/2000 | Drobot et al. | 250/234 |
| 6,096,054 | A | 8/2000 | Wyzgala et al. | 606/170 |
| 6,097,528 | A | 8/2000 | Lebby et al. | 359/251 |
| 6,134,003 | A | 10/2000 | Tearney et al. | 356/345 |
| 6,142,957 | A | 11/2000 | Diamond et al. | 600/567 |
| 6,148,095 | A | 11/2000 | Prause et al. | 382/131 |
| 6,161,035 | A | 12/2000 | Furusawa | 600/476 |
| 6,169,281 | B1 | 1/2001 | Chen et al. | 250/234 |
| 6,185,443 | B1 | 2/2001 | Crowley | 600/407 |
| 6,191,862 | B1 | 2/2001 | Swanson et al. | 356/450 |
| 6,211,904 | B1 | 4/2001 | Adair et al. | 348/76 |
| 6,215,437 | B1 | 4/2001 | Schurmann et al. | 342/42 |
| 6,240,312 | B1 | 5/2001 | Alfano et al. | 600/476 |
| 6,241,657 | B1 | 6/2001 | Chen et al. | 600/117 |
| 6,246,914 | B1 | 6/2001 | de la Rama et al. | 607/122 |
| 6,289,144 | B1 | 9/2001 | Neuschafer et al. | 385/12 |
| 6,294,775 | B1 | 9/2001 | Seibel et al. | 250/208.1 |
| 6,327,493 | B1 | 12/2001 | Ozawa et al. | 600/476 |
| 6,370,422 | B1 | 4/2002 | Richards-Kortum et al. | 600/478 |
| 6,387,119 | B2 | 5/2002 | Wolf et al. | 623/1.11 |
| 6,441,359 | B1 | 8/2002 | Cozier et al. | 250/216 |
| 6,443,894 | B1 | 9/2002 | Sumanaweera et al. | 600/443 |
| 6,461,337 | B1 | 10/2002 | Minotti et al. | 604/264 |
| 6,466,687 | B1 | 10/2002 | Uppaluri et al. | 382/128 |
| 6,477,295 | B1 * | 11/2002 | Lang et al. | 385/31 |
| 6,485,413 | B1 | 11/2002 | Boppart et al. | 600/160 |
| 6,501,875 | B2 * | 12/2002 | Zhao et al. | 385/30 |
| 6,515,274 | B1 | 2/2003 | Moskovits et al. | 250/216 |
| 6,515,781 | B2 | 2/2003 | Lewis et al. | 359/204 |
| 6,525,310 | B2 | 2/2003 | Dunfield | 250/235 |
| 6,545,260 | B1 | 4/2003 | Katashiro | 250/227.26 |
| 6,546,271 | B1 | 4/2003 | Reisfeld | 600/407 |
| 6,549,801 | B1 | 4/2003 | Chen et al. | 600/425 |
| 6,550,918 | B1 | 4/2003 | Agostinelli et al. | 353/7 |
| 6,563,105 | B2 * | 5/2003 | Seibel et al. | 250/208.1 |
| 6,563,998 | B1 | 5/2003 | Farah et al. | 385/131 |
| 6,564,087 | B1 | 5/2003 | Pitris et al. | 600/478 |
| 6,564,089 | B2 | 5/2003 | Izatt et al. | 600/478 |
| 6,608,951 | B1 * | 8/2003 | Goldberg et al. | 385/43 |
| 6,612,980 | B2 | 9/2003 | Chen et al. | 600/117 |
| 6,615,072 | B1 | 9/2003 | Izatt et al. | 600/478 |
| 6,678,541 | B1 | 1/2004 | Durkin et al. | 600/310 |
| 6,685,718 | B1 | 2/2004 | Wyzgala et al. | 606/170 |
| 6,687,010 | B1 | 2/2004 | Horii et al. | 356/479 |
| 6,687,445 | B2 * | 2/2004 | Carter et al. | 385/127 |
| 6,689,064 | B2 | 2/2004 | Hager et al. | 600/454 |
| 6,690,963 | B2 | 2/2004 | Ben-Haim et al. | 600/424 |
| 6,694,983 | B2 | 2/2004 | Wolf et al. | 128/898 |
| 6,731,837 | B2 * | 5/2004 | Goldberg et al. | 385/27 |
| 6,735,463 | B2 | 5/2004 | Izatt et al. | 600/476 |
| 6,744,948 | B1 * | 6/2004 | Pi et al. | 385/30 |
| 6,755,532 | B1 | 6/2004 | Cobb | 353/7 |
| 6,773,394 | B2 | 8/2004 | Taniguchi et al. | 600/117 |
| 6,779,892 | B2 | 8/2004 | Agostinelli et al. | 353/7 |
| 6,785,571 | B2 | 8/2004 | Glossop | 600/424 |
| 6,788,967 | B2 | 9/2004 | Ben-Haim et al. | 600/424 |
| 6,818,001 | B2 | 11/2004 | Wulfman et al. | 606/159 |
| 6,826,342 | B1 | 11/2004 | Bise et al. | 385/125 |
| 6,832,984 | B2 | 12/2004 | Stelzer et al. | 604/93.01 |
| 6,836,560 | B2 | 12/2004 | Emery | 382/145 |
| 6,839,586 | B2 | 1/2005 | Webb | 600/478 |
| 6,845,190 | B1 | 1/2005 | Smithwick et al. | 385/25 |
| 6,856,712 | B2 * | 2/2005 | Fauver et al. | 385/12 |
| 6,858,005 | B2 | 2/2005 | Ohline et al. | 600/141 |
| 6,872,433 | B2 | 3/2005 | Seward et al. | 428/36.9 |
| 6,882,429 | B1 | 4/2005 | Weitekamp et al. | 356/482 |
| 6,889,175 | B2 | 5/2005 | Green | 702/190 |
| 6,892,090 | B2 | 5/2005 | Verard et al. | 600/424 |
| 6,895,270 | B2 | 5/2005 | Ostrovsky | 600/476 |
| 6,902,528 | B1 | 6/2005 | Garibaldi et al. | 600/118 |
| 6,932,829 | B2 | 8/2005 | Majercak | 606/198 |
| 6,975,898 | B2 * | 12/2005 | Seibel | 600/473 |
| 7,004,173 | B2 | 2/2006 | Sparks et al. | 128/898 |
| 7,023,558 | B2 | 4/2006 | Fee et al. | 356/489 |

(56) References Cited

U.S. PATENT DOCUMENTS

| | | | |
|---|---|---|---|
| 7,038,191 B2 | 5/2006 | Kare et al. | 250/227.11 |
| 7,065,279 B2* | 6/2006 | Shima et al. | 385/123 |
| 7,068,878 B2* | 6/2006 | Crossman-Bosworth et al. | 385/25 |
| 7,072,046 B2 | 7/2006 | Xie et al. | 356/479 |
| 7,158,234 B2 | 1/2007 | Uchiyama et al. | 356/479 |
| 7,170,610 B2 | 1/2007 | Knuttel | 356/456 |
| 7,179,220 B2 | 2/2007 | Kukuk | 600/118 |
| 7,189,961 B2 | 3/2007 | Johnston et al. | 250/234 |
| 7,252,674 B2 | 8/2007 | Wyzgala et al. | 606/170 |
| 7,261,687 B2 | 8/2007 | Yang | 600/173 |
| 7,324,211 B2 | 1/2008 | Tsujita | 356/497 |
| 7,349,098 B2 | 3/2008 | Li | 356/479 |
| 7,366,376 B2 | 4/2008 | Shishkov et al. | 385/35 |
| 7,404,929 B2 | 7/2008 | Fulghum, Jr. | 422/82.05 |
| 7,447,408 B2 | 11/2008 | Bouma et al. | 385/123 |
| 7,515,274 B2 | 4/2009 | Gelikonov et al. | 356/479 |
| 7,530,948 B2 | 5/2009 | Seibel et al. | 600/102 |
| 7,615,005 B2 | 11/2009 | Stefanchik et al. | 600/106 |
| 7,616,986 B2 | 11/2009 | Seibel et al. | 600/476 |
| 7,747,312 B2 | 6/2010 | Barrick et al. | 600/426 |
| 7,783,337 B2 | 8/2010 | Feldman et al. | 600/160 |
| 2001/0030744 A1 | 10/2001 | Chang et al. | 356/73 |
| 2001/0055462 A1* | 12/2001 | Seibel | 385/147 |
| 2002/0071625 A1 | 6/2002 | Bartholomew et al. | 385/12 |
| 2003/0009189 A1 | 1/2003 | Gilson et al. | 606/200 |
| 2003/0032878 A1 | 2/2003 | Shahidi | 600/429 |
| 2003/0045778 A1 | 3/2003 | Ohline et al. | 600/114 |
| 2003/0055317 A1 | 3/2003 | Taniguchi et al. | 600/117 |
| 2003/0103199 A1 | 6/2003 | Jung et al. | 356/73 |
| 2003/0103665 A1 | 6/2003 | Uppaluri et al. | 382/131 |
| 2003/0142934 A1 | 7/2003 | Pan et al. | 385/115 |
| 2003/0160721 A1 | 8/2003 | Gilboa et al. | 342/450 |
| 2003/0179428 A1 | 9/2003 | Suzuki et al. | 359/204 |
| 2003/0208107 A1 | 11/2003 | Refael | 600/300 |
| 2003/0208134 A1 | 11/2003 | Secrest et al. | 600/562 |
| 2003/0216639 A1 | 11/2003 | Gilboa et al. | 600/424 |
| 2003/0220749 A1 | 11/2003 | Chen et al. | 702/31 |
| 2003/0236564 A1 | 12/2003 | Majercak | 623/1.11 |
| 2004/0015049 A1 | 1/2004 | Zaar | 600/101 |
| 2004/0015053 A1 | 1/2004 | Bieger et al. | 600/117 |
| 2004/0033006 A1 | 2/2004 | Farah | 385/14 |
| 2004/0061072 A1 | 4/2004 | Gu et al. | 250/458.1 |
| 2004/0114860 A1* | 6/2004 | Dultz et al. | 385/31 |
| 2004/0114865 A1* | 6/2004 | Ryall et al. | 385/39 |
| 2004/0118415 A1 | 6/2004 | Hall et al. | 128/898 |
| 2004/0147827 A1 | 7/2004 | Bowe | 600/374 |
| 2004/0176683 A1 | 9/2004 | Whitin et al. | 600/424 |
| 2004/0181148 A1 | 9/2004 | Uchiyama et al. | 600/425 |
| 2004/0199052 A1 | 10/2004 | Banik et al. | 600/102 |
| 2004/0240819 A1* | 12/2004 | Shima et al. | 385/126 |
| 2004/0243227 A1 | 12/2004 | Starksen et al. | 623/2.11 |
| 2004/0249267 A1 | 12/2004 | Gilboa | 600/204 |
| 2004/0254474 A1* | 12/2004 | Seibel et al. | 600/473 |
| 2004/0260199 A1 | 12/2004 | Hardia et al. | 600/566 |
| 2005/0020878 A1 | 1/2005 | Ohnishi et al. | 600/117 |
| 2005/0020926 A1 | 1/2005 | Wiklof et al. | 600/476 |
| 2005/0036150 A1 | 2/2005 | Izatt et al. | 356/479 |
| 2005/0054931 A1 | 3/2005 | Clark | 600/453 |
| 2005/0065433 A1 | 3/2005 | Anderson | 600/424 |
| 2005/0085693 A1 | 4/2005 | Belson et al. | 600/146 |
| 2005/0111009 A1 | 5/2005 | Keightley et al. | 356/602 |
| 2005/0117860 A1* | 6/2005 | Vienne et al. | 385/115 |
| 2005/0168751 A1 | 8/2005 | Horii et al. | 356/479 |
| 2005/0171438 A1 | 8/2005 | Chen et al. | 600/476 |
| 2005/0171592 A1 | 8/2005 | Majercak | 623/1.11 |
| 2005/0183733 A1 | 8/2005 | Kawano et al. | 128/899 |
| 2005/0206774 A1 | 9/2005 | Tsujimoto | 348/345 |
| 2005/0215854 A1 | 9/2005 | Ozaki et al. | 600/109 |
| 2005/0215911 A1 | 9/2005 | Alfano et al. | 600/476 |
| 2005/0228290 A1 | 10/2005 | Borovsky et al. | 600/466 |
| 2005/0250983 A1 | 11/2005 | Tremaglio et al. | 600/101 |
| 2005/0272975 A1 | 12/2005 | McWeeney et al. | 600/113 |
| 2006/0013544 A1* | 1/2006 | Bouma et al. | 385/116 |
| 2006/0015126 A1 | 1/2006 | Sher | 606/159 |
| 2006/0030753 A1 | 2/2006 | Boutillette et al. | 600/146 |
| 2006/0052662 A1 | 3/2006 | Kress | 600/123 |
| 2006/0100480 A1 | 5/2006 | Ewers et al. | 600/114 |
| 2006/0126064 A1 | 6/2006 | Bambot et al. | 356/337 |
| 2006/0149134 A1 | 7/2006 | Soper et al. | 600/182 |
| 2006/0149163 A1 | 7/2006 | Hibner et al. | 600/566 |
| 2006/0187462 A1 | 8/2006 | Srinivasan et al. | 356/479 |
| 2006/0202115 A1 | 9/2006 | Lizotte et al. | 250/234 |
| 2006/0252993 A1 | 11/2006 | Freed et al. | 600/146 |
| 2007/0038119 A1 | 2/2007 | Chen et al. | 600/476 |
| 2007/0066983 A1 | 3/2007 | Maschke | 606/159 |
| 2007/0088219 A1 | 4/2007 | Xie et al. | 600/473 |
| 2007/0093703 A1 | 4/2007 | Sievert et al. | 600/343 |
| 2007/0129601 A1 | 6/2007 | Johnston et al. | 600/109 |
| 2007/0213618 A1 | 9/2007 | Li et al. | 600/476 |
| 2007/0230881 A1* | 10/2007 | Tammela et al. | 385/115 |
| 2007/0270650 A1 | 11/2007 | Eno et al. | 600/145 |
| 2008/0004491 A1 | 1/2008 | Karasawa | 600/101 |
| 2008/0107384 A1* | 5/2008 | Nadolski | 385/115 |
| 2008/0221388 A1 | 9/2008 | Seibel et al. | 600/109 |

FOREIGN PATENT DOCUMENTS

| | | | |
|---|---|---|---|
| EP | 0 520 388 | 9/1996 | B41J 2/455 |
| EP | 1 077 360 | 2/2001 | G01B 9/02 |
| EP | 1 088 515 | 4/2001 | A61B 5/06 |
| EP | 1 142 529 | 10/2001 | A61B 1/00 |
| EP | 0 712 032 | 12/2001 | G03B 35/08 |
| EP | 1 310 206 | 5/2003 | A61B 1/015 |
| EP | 1 421 913 | 5/2004 | A61B 19/00 |
| EP | 0 910 284 | 1/2007 | A61B 10/00 |
| EP | 1 063 921 | 2/2007 | A61B 10/00 |
| JP | 05-154154 | 6/1993 | A61B 10/00 |
| JP | 06-511312 | 12/1994 | G01B 9/02 |
| JP | 2000-275451 | 10/2000 | |
| JP | 2000275451 A * | 10/2000 | G02B 6/10 |
| JP | 2001174744 | 6/2001 | G02B 23/24 |
| JP | 2003-535659 | 12/2003 | |
| JP | 2005-283917 | 10/2005 | |
| JP | 2005283917 A * | 10/2005 | G02B 6/04 |
| WO | WO 93/20742 | 10/1993 | A61B 1/06 |
| WO | WO 96/02184 | 2/1996 | A61B 5/00 |
| WO | WO 98/38907 | 9/1998 | A61B 5/00 |
| WO | WO 98/43530 | 10/1998 | A61B 1/00 |
| WO | WO 99/04301 | 1/1999 | G02B 21/00 |
| WO | WO 01/97902 | 12/2001 | |
| WO | WO 2005/024496 | 3/2005 | |

OTHER PUBLICATIONS

Barnard et al., "Mode Transforming Properties of Tapered Single-mode Fiber Microlens." *Appl. Opt.* vol. 32, No. 12: 2090-2094, Apr. 20, 1993.

Barnard et al., "Single-mode Fiber Microlens with Controllable Spot Size." *Appl. Opt.* vol. 30, No. 15: 1958-1962, May 20, 1991.

Bird et al., "Two-photon fluorescence endoscopy with a micro-optic scanning head." *Optics Letters*, vol. 28, No. 17: 1552-1554, 2003.

Borreman et al., "Fabrication of Polymeric Multimode Waveguides and Devices in SU-8 Photoresist Using Selective Polymerization." *Proceedings Symposium IEEE/LEOS Benelux Chapter*, Amsterdam: pp. 83-86, 2002.

Brown et al., "Recognising Panoramas." *Proceedings of the Ninth IEEE International Conference on Computer Vision* 8pp., Apr. 2003.

Chen et al., "Dispersion management up to the third order for real-time optical coherence tomography involving a phase or frequency modulator." *Optics Express* vol. 12, No. 24: 5968-5978, 2004.

Chen et al., "Optical Doppler tomographic imaging of fluid flow velocity in highly scattering media." *Optics Letters*, vol. 22, No. 1: 64-66, 1997.

Clark et al., "Fiber delivery of femtosecond pulses from a Ti:sapphire laser." *Optics Letters*, vol. 26, No. 17: 1320-1322, 2001.

Deschamps et al., "Automatic construction of minimal paths in 3D images: An application to virtual endoscopy." *CARS'99*—H. U Lemke, M.W. Vannier, K. Inamura & A.G. Fannan (Editors) *Elsevier Science B.V.*: 151-155, 1999.

(56) References Cited

OTHER PUBLICATIONS

Dickensheets et al., "A Scanned Optical Fiber Confocal Microscope." *Three-Dimensional Microscopy* SPIE vol. 2184: 39-47, 1994.

Dickensheets et al., "Micromachined scanning confocal optical microscope." *Optics Letters*, vol. 21, No. 10: 764-766, May 15, 1996.

Drexler et al., "In vivo ultrahigh-resolution optical coherence tomography." *Optics Letters*, vol. 24, No. 17: 1221-1223, 1999.

Finci et al., "Tandem balloon catheter for coronary angioplasty." *Catheter Cardiovascular Diagnosis* vol. 12, No. 6: 421-425, 1986. 2pp Abstract.

Flusberg et al., "In vivo brain imaging using a portable 3.9 gram two-photon fluorescence microendoscope." *Optics Letters*, vol. 30, No. 17: 2272-2274. 2005.

Fu et al., "Nonlinear optical microscopy based on double-clad photonic crystal fibers." *Optics Express* vol. 13, No. 14: 5528-5534 + supplemental page, 2005.

Göbel et al., "Miniaturized two-photon microscope based on a flexible coherent fiber bundle and a gradient-index lens objective." *Optics Letters*, vol. 29, No. 21: 2521-2523, 2004.

Helmchen et al., "A Miniature Head-Mounted Two-Photon Microscope: High Resolution Brain Imaging in Freely Moving Animals." *NEURON* vol. 31: 903-912, Sep. 27, 2001.

Herline et al., "Surface Registration for Use in Interactive, Image-Guided Liver Surgery." *Computer Aided Surgery*, vol. 5: 11-17, 1999.

Higgins et al., "Integrated Bronchoscopic Video Tracking and 3D CT Registration for Virtual Bronchoscopy." *Medical Imaging* 2003, vol. 5031: 80-89, 2003.

Huang et al., "Optical Coherence Tomography." *Science* vol. 254, Issue 5035: 1178-1181, 1991.

Huber et al., "Amplified, frequency swept lasers for frequency domain reflectometry and OCT imaging: design and scaling principles." *Optics Express* vol. 13, No. 9: 3513-3528, May 2, 2005.

Jung et al., "Multiphoton endoscopy." *Optics Letters*, vol. 28, No. 11: 902-904, 2003.

Kiesslich et al., "Diagnosing *Helicobacter pylori* in Vivo by Confocal Laser Endoscopy." *Gastroenterology* vol. 128: 2119-2123, 2005.

Kiraly et al., "Three-Dimensional Path Planning for Virtual Bronchoscopy." *IEEE Transactions on Medical Imaging*, vol. 23, No. 9: 1365-1379, Sep. 2004.

Lee et al., "Microlenses on the End of Single-mode Optical Fibers for Laser Applications." *Appl. Opt.* vol. 24, No. 19: 3134-3139, Oct. 1, 1985.

Lewis et al., "Scanned beam medical imager." *MOEMS Display and Imaging System II*, edited by Hakan Urey, David L. Dickensheets, Proceedings of SPIE, Bellingham, WA, vol. 5348: 40-51, 2004.

Lexer et al., "Dynamic coherent focus OCT with depth-independent transversal resolution." *Journal of Modern Optics* vol. 46, No. 3: 541-553, 1999.

Li et al., "Optical Coherence Tomography: Advanced Technology for the Endoscopic Imaging of Barrett's Esophagus" *Endoscopy*, vol. 32, No. 12: 921-930, 2000.

Liu et al., "3D Navigation for Endoscope by Magnetic Field." *Proceedings of SPIE*, vol. 4556 25-28, 2001.

Liu et al., "Rapid-scanning forward-imaging miniature endoscope for real-time optical coherence tomography." *Optics Letters*, vol. 29, No. 15: 1763-1765, 2004.

Martinez, O.E., "3000 Times Grating Compressor with Positive Group-Velocity Dispersion—Application to Fiber Compensation in 1.3-1.6 μm Region." *IEEE Journal of Quantum Electronics* vol. 23: 59-64, 1987.

Mori et al., "A Method for Tracking camera motion of real endoscope by using virtual endoscopy system." *Proceedings of SPIE*: 1-12, 2000. <www.http://www.toriwaki.nuie.nagoya-u.ac.jp> 12pp. 1-12.

Morofke et al., "Wide dynamic range detection of bidirectional flow in Doppler optical coherence tomography using a two-dimensional Kasai estimator." *Optics Letters*, vol. 32, No. 3: 253-255, Feb. 1, 2007.

Murakami et al., "A Miniature Confocal Optical Microscope With Mems Gimbal Scanner." *The 12th International Conference on Solid State Sensors, Actuators and Microsystems* Boston: 587-590, Jun. 8-12, 2003.

Myaing et al., "Enhanced two-photon biosensing with double-clad photonic crystal fibers," *Optics Letters*, vol. 28, No. 14: 1224-1226, 2003.

Brunetaud, Jean Marc, Vincent Maunoury, and Dominique Cochelard. "Lasers in Digestive Endoscopy," Journal of Biomedical Optics 2(1), 42-52 (Jan. 1997).

\* cited by examiner

MULTI-CLADDING OPTICAL FIBER SCANNER

GOVERNMENT RIGHTS

This invention was made with U.S. Government support under grant number CA094303-R33 awarded by the National Institute of Health (NIH). The U.S. Government has certain rights in the invention.

BACKGROUND

The maximum transmissible optical power in a high-resolution scanning fiber endoscope system is limited by the requirement for small-core singlemode light propagation. The generally accepted threshold for material damage of a singlemode silica optical fiber is about 1 $MW/cm^2$ for solid fiber and higher thresholds for photonics crystal or microstructured singlemode optical fibers. Thus, using an optical fiber that has a mode field diameter of 3.5 microns limits the optical power that can be delivered for therapy to a maximum of about 100 mW, when a conventional single resonant optical fiber is employed for both imaging and therapy. This level of power can easily be provided in the visible wavelengths by currently available diode-pumped solid-state or argon-ion gas lasers, and by high-power ultraviolet laser diodes and ultraviolet lasers that are being developed. Use of light in the visible range of wavelengths is desirable for rendering therapy in current configurations that employ the same optical fiber for both imaging and therapy, because of the potential for increased bending and launching losses that occur if infrared (IR) wavelengths are used in a visible wavelength optical fiber, or if shorter wavelength ultraviolet light is used in conventional multimode optical fiber scanners. Although tissue absorption levels are low in the visible range, it is expected that this amount of power will enable some limited therapeutic capability.

However, in the case where higher levels of optical power are needed for advanced levels of therapy, the existing scanning fiber endoscope design does not provide sufficient power handling capability. This problem only becomes an issue if it is necessary to both image and provide therapy to an internal site. If one or more fixed optical fibers are used to provide therapy, the nature and quantity of the therapeutic fibers and laser sources can be selected solely on the basis of therapeutic effect, with no regard to imaging. For example, the most commonly used laser in digestive endoscopy is the Nd:YAG laser which emits light at 1.06 micron wavelength that is usually conveyed to the tissues by a sheathed optical fiber within the working channel of the endoscope or within a cannula alongside the endoscope (Brunetaud, J. M., Maunoury, V., and Cochelard, D., Lasers in Digestive Endoscopy, Journal of Biomedical Optics 2(1): 42-52 January 1997). To deliver these much greater optical power levels, large-core multimode optical fibers would typically be used, rather than the small-core, singlemode optical fiber that is required for high-resolution imaging. To deliver more than fixed spots of laser irradiation to an imaged field, the separate large-core optical fiber(s) must be inserted through a larger endoscope within a working channel or secondary cannula that allows moving delivery of the optical therapeutic dosage across the stationary endoscopic field by hand. A drawback to this approach is that additional channels are required for combining imaging and therapy for minimally-invasive medicine.

One advantage of employing a dedicated fixed fiber configuration for a separate therapy channel is that it can operate at optical powers below the material damage threshold and still deliver sufficient power to perform a broad range of laser therapies. The disadvantage of such a configuration, however, is that the resulting endoscope system is more bulky and more invasive to the patient. Therefore, it would be desirable to provide a configuration for an endoscope system that can achieve maximal power operation in one single illumination fiber endoscope to provide the desired optical power therapeutic capacity, while also enabling imaging (and perhaps diagnostic) procedures to be conducted of the site to which the optical therapy is to be delivered. A compact single optical fiber endoscope with such properties has not yet been commercially available.

SUMMARY

In consideration of the preceding concerns, a relatively compact endoscopic apparatus has been developed for both imaging a site within a patient's body and rendering therapy to the site. An example of the most basic apparatus includes a dual-cladding optical fiber having a core, an inner cladding, and an outer cladding, all extending generally between a proximal end and a distal end. An imaging light source produces imaging light for use in illuminating a site within a patient's body, so that an image of the site can be viewed on a display screen. The imaging light is directed into the core of the dual-cladding optical fiber at the proximal end and is conveyed to the distal end of the dual-cladding optical fiber, where it is emitted toward the site to be imaged. A therapy light source is provided to produce therapy light having a substantially greater power than the imaging light. The therapy light is directed into the inner cladding at the proximal end and is conveyed to the distal end of the dual-cladding optical fiber, where it is used to render therapy to a desired region at a site. An actuator is disposed adjacent to the distal end of the dual-cladding optical fiber and is selectively energized so as to move the distal end of the core and the inner cladding in a desired path. When imaging the site, the moving distal end of the core is caused to move in the desired path so as to scan the site with the imaging light to illuminate it. Similarly, while rendering therapy to a desired region of the site, the moving inner cladding emits therapy light that is directed toward and over the desired region. At least one sensor is provided for receiving light from the site that is being imaged and produces a signal useful for creating an image of the site in response to the light received therefrom, for example, in response to the imaging light that is reflected from the site.

The apparatus of at least one embodiment further includes a housing disposed at the distal end of the dual-cladding optical fiber. The housing supports a lens system for focusing the imaging light and the therapy light emitted from the distal end of the dual-cladding optical fiber onto the site. Further, the at least one sensor can be disposed adjacent to the distal end of the dual-cladding optical fiber and supported by the housing to receive light from the site. In this case, the signal produced by the at least one sensor can be conveyed through at least one electrical lead that extends generally to the proximal end of the dual-cladding optical fiber.

Alternatively, at least one additional optical fiber can be included in the apparatus for conveying light received from the site toward the proximal end of the dual-cladding optical fiber. In this alternative embodiment, the at least one sensor is preferably disposed adjacent to the proximal end of the dual-cladding optical fiber and is coupled to the at least one additional optical fiber to receive the light from the site that was conveyed through the additional optical fiber.

In one form of the apparatus, an axicon is included for coupling the therapy light from the therapy light source into the inner cladding of the dual-cladding optical fiber, at the proximal end thereof, while enabling the imaging light from the imaging light source to be directed into the core of the dual-cladding optical fiber.

Other embodiments include a proximal lens system for focusing at least one of the therapy light (into the inner cladding), and the imaging light (into the core). In one embodiment, the proximal lens system includes a reflective surface. This reflective surface reflects either or both the therapy light (into the inner cladding), and the imaging light (into the core).

In yet another embodiment, an outer cladding is removed from a segment of the dual-cladding optical fiber adjacent to the proximal end, exposing the inner cladding within the segment. In this embodiment, the lens system directs the therapy light into the inner cladding at the segment, so that the therapy light is conveyed through the inner cladding toward the distal end of the dual-cladding optical fiber.

Still another embodiment includes a multimode optical fiber that is coupled to the therapy light source to receive the therapy light. The cladding is removed from a segment of the multimode optical fiber, exposing a multimode core that conveys the therapy light. An outer cladding is also removed from a segment of the dual-cladding optical fiber, exposing the inner cladding, but not disrupting the core. The inner cladding at this segment is also polished and affixed in contact with the multimode core that is polished, thereby facilitating transfer of the therapy light from the multimode core into the inner cladding. A fixture is preferably used to support the multimode core that is polished in a light coupling relationship with the inner cladding of the dual-cladding optical fiber that is polished.

Another embodiment includes a proximal lens system, and a reflective surface. The outer cladding and the inner cladding are removed from a segment of the dual-cladding optical fiber adjacent to the proximal end, forming a gap around the core. The reflective surface is then disposed in the gap, and the proximal lens system focuses the therapy light toward the reflective surface, which reflects the therapy light into an end of the inner cladding comprising one side of the gap. The therapy light is thus directed toward the distal end of the dual-cladding optical fiber within the inner cladding.

Another aspect of the present development is directed to a method for enabling imaging of a site within a patient's body and providing optical therapy to the site. The method includes steps that are generally consistent with the functionality of the elements in the different embodiments of the apparatus discussed above.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive.

Exemplary Scanning Device

Figure 1A:
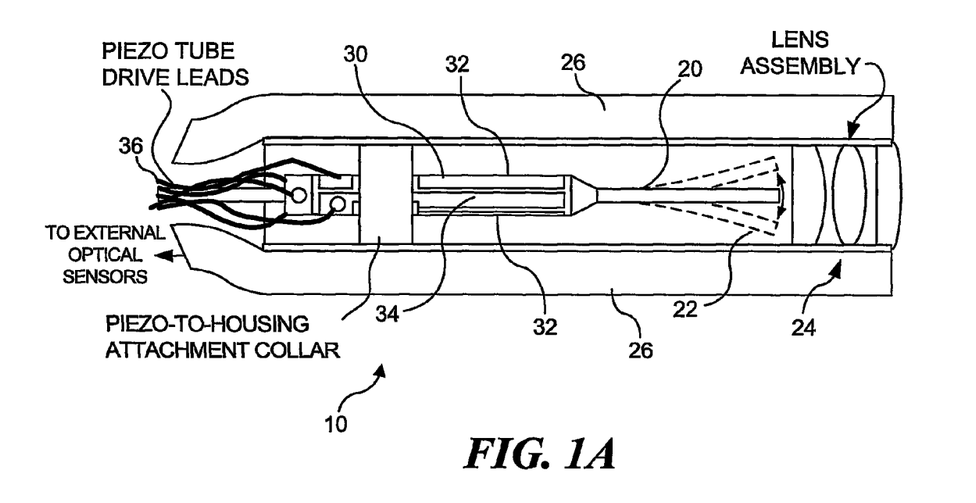
FIG. 1A illustrates an exemplary scanning device having a dual-cladding optical fiber that can be driven to scan a region in a variable radius circular, or spiral scanning mode, and when imaging the region, collects light through a plurality of optical sensors or optical fibers disposed around a window at the distal end of the scanning device.

An exemplary optical fiber device 10, which is drivable in a variable linear or elliptical scan mode and is useful for both imaging an internal site and rendering therapy to the internal site as discussed below, is illustrated in FIG. 1A. The scan mode shown in this figure can be generated by driving an optical fiber cantilever 20 that comprises a dual-cladding optical fiber, into a resonant (or near-resonant) condition using, for example, a piezoceramic tube actuator 30. A single-axis (linear) scan pattern 22 can be generated by applying voltage on one or opposing electrodes of an actuator 32. By applying an oscillating voltage (e.g., a sine wave) at or near the mechanical resonant frequency of the base-excited fiber cantilever to the piezoceramic tube actuator through piezo tube electrical leads 36, the amplitude of the tip motion can be mechanically amplified due to the mechanical resonance of the fiber cantilever. For example, the concurrent application of a second sinusoidal voltage (cosine wave) to the second orthogonal set of electrodes 34 on the actuator, at the same or slightly different resonant frequency, causes the resonating fiber tip to move in an elliptical pattern.

An image is generated by the fiber scanner shown in FIG. 1A by focusing the light from the scanned distal tip of the fiber using imaging lenses 24. Typically, the imaging lenses focus and magnify the scanned point source from the scanning fiber tip to the region of interest (ROI) in either the linear (one-dimensional) or elliptical (two-dimensional) patterns. By varying the amplitude of the voltages applied to the actuator during the elliptical scan, a two-dimensional (2-D) space-filling illumination pattern is formed. Light collection optical fibers 26 that surround the fiber scanner are used to collect the backscattered illumination light that provides the signal for generating the 2-D image in a time series (one pixel at a time). Typically, light collection optical fibers 26 are large-core and high-numerical aperture, multimode optical fibers for the purpose of increasing light collection efficiency. In contrast, optical fiber cantilever 20, which is used for the scanned illumination, is a dual-cladding optical fiber having a small diameter singlemode core surrounded by an inner cladding, which in turn, is surrounded by an outer cladding, as described in greater detail below.

Figure 1B:
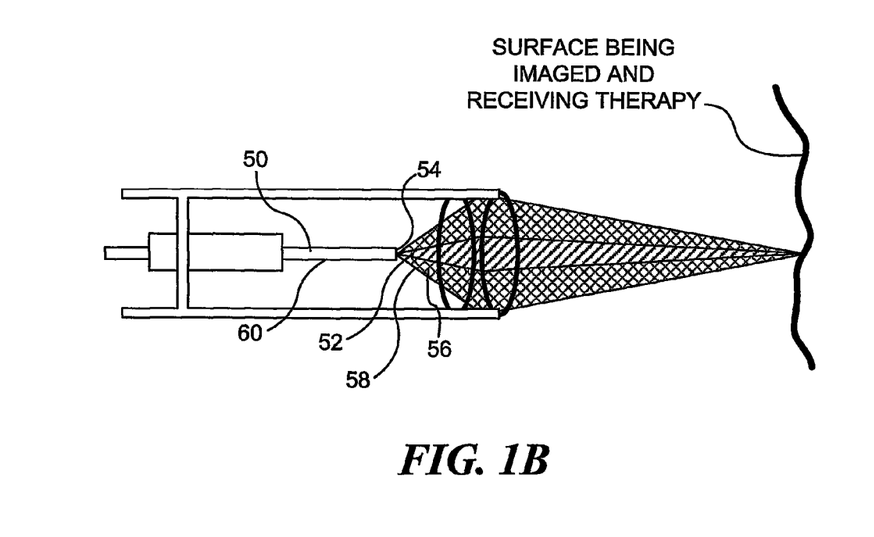
FIG. 1B illustrates an exemplary scanning device that emits visible light from the core of a singlemode dual-cladding optical fiber when imaging an adjacent surface and emits relatively high-intensity light (e.g., infrared (IR) light) that is conveyed through an inner cladding of the dual-cladding optical fiber, when providing optical therapy to the surface.

As illustrated in FIG. 1B, the distal tip of a stationary dual-clad optical fiber 50 is shown to have a small core diameter 52. The numerical aperture of the core is shown as a cone, with its vertex at a core end face 54. The inner cladding region of the dual-clad optical fiber typically has a much larger diameter 56 and has a higher numerical aperture, as shown by a larger cone angle 58, the outer cladding layer is often a thin polymer coating 60 of a lowest refractive index.

Figures 1C, 3A:
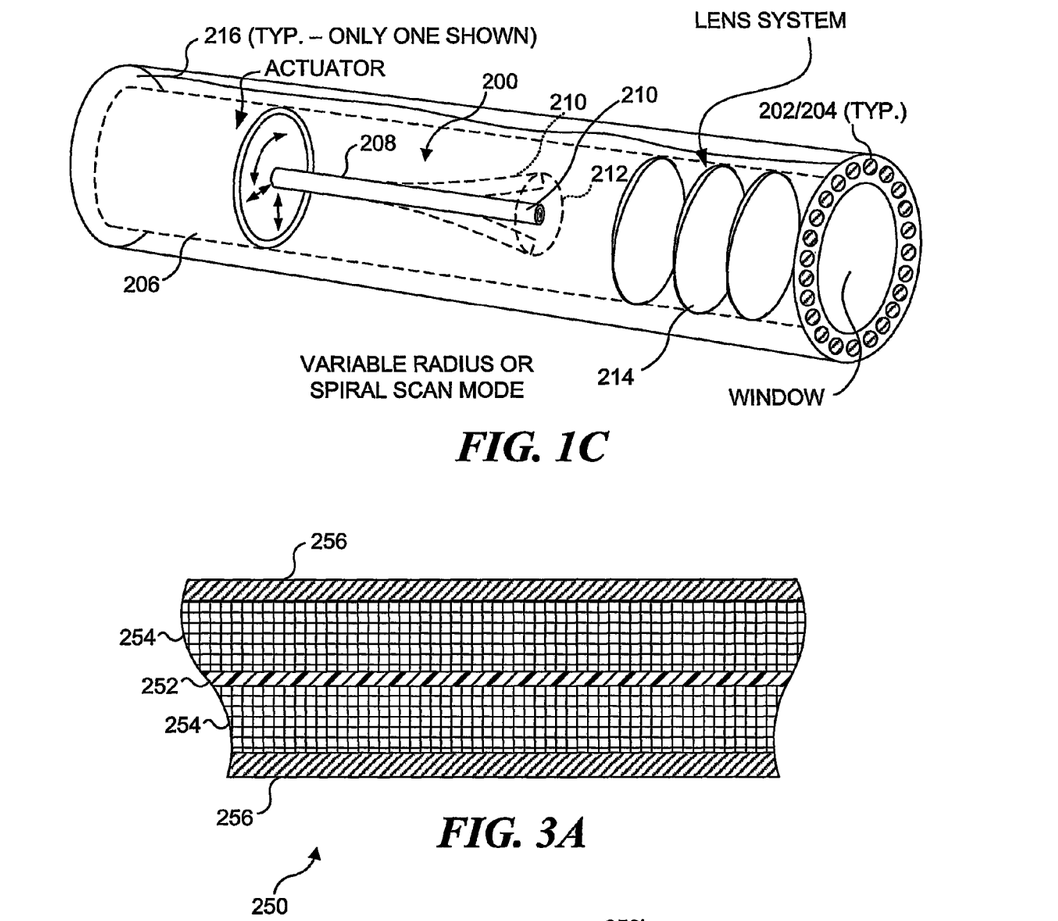
FIG. 1C illustrates further details of an exemplary scanning device having a dual-cladding optical fiber that can be driven to scan a region in a variable radius circular, or spiral scanning mode, and when imaging the region, collects light through a plurality of optical sensors or optical fibers disposed around a window at the distal end of the scanning device.
FIG. 3A is a longitudinal cross-sectional view of a dual-cladding optical fiber suitable for use in connection with the approach disclosed below.

A cut-away view in FIG. 1C illustrates a variable radius or spiral scan mode of an optical fiber device 200. The scan mode shown in this Figure can be generated by driving a dual-cladding optical fiber 208 into a resonant (or near-resonant) condition using a two-axis piezoceramic tube actuator 206. In this exemplary embodiment, a plurality of light detectors 204 are arrayed around single piezoceramic tube actuator 206 in a simple arrangement, to produce signals conveyed over electrical leads 216 (only one shown) indicative of the light received from an ROI, which is not shown in this Figure. Alternatively, a similar array of concentrically arranged and spaced-apart optical fibers 202 can convey light received at the distal end of the optical fibers from the ROI to light detectors (not shown) that are disposed at a proximal end of the optical fibers (e.g., outside the body of a patient). Piezoceramic tube actuator 206 concentrically surrounds dual-cladding optical fiber 208. This tube actuator produces a driving force corresponding to a harmonic of a natural resonant frequency of optical fiber 208 so that distal end 210 of the optical fiber moves in an orbit 212 having an actuation controlled radius. The distal end of the scanning optical fiber corresponds to an optical point source that can be focused onto an illumination plane (not shown) by adding an imaging lens system 214. A major advantage of this embodiment is that it employs a single actuator and a waveguide that provide high-resolution, directed illumination, and imaging within a relatively small diameter enclosure.

A series of variable radii circles are produced in a circular scan mode. The optical fiber can be driven in either mode during successive scanning frames. When driven in a spiral scan mode, the optical fiber produces a spiral scan in which the radius alternately increases and decreases. In an alternative scan pattern, the radius is increased in the desired pattern, and then the fiber is more rapidly returned to its centered position to begin the next frame. In either the circular or spiral scan modes, the distal end of optical fiber 208 scans an ROI to image the region and also renders therapy and/or diagnostic functions to the ROI. The whirling motion of the cantilevered optical fiber is controllably driven larger or smaller in diameter by increasing or decreasing the voltage applied to the four individual quadrants of piezoceramic tube actuator 206. Changes in the diameter of the scan can thus be made in successive scanning frames. When imaging an adjacent site within a patient's body, the diameter of the scan may be made greater to encompass a larger area in one scan frame, and in a subsequent scanning frame, can be reduced, when rendering therapy only to a small portion of the imaged area.

Exemplary Scanning System

Figure 2:
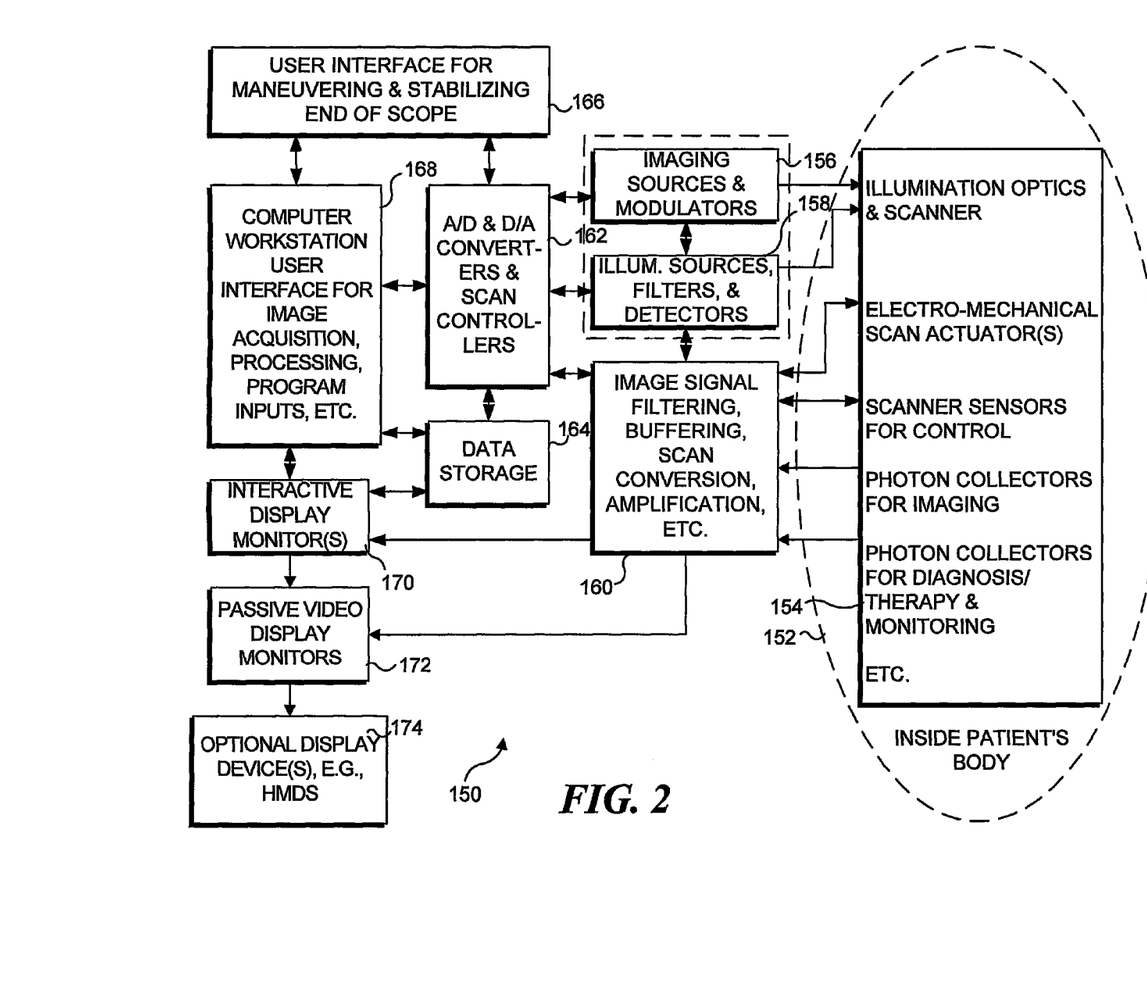
FIG. 2 is a block diagram illustrating the functional flow of signals in a system that is usable with a scanning device employing a dual-cladding optical fiber as described herein, for any of imaging, monitoring, and rendering diagnoses, and also for providing therapy to a region.

FIG. 2 illustrates a system 150 that shows how the signals produced by various components that are inside a patient's body are processed with external instrumentation, and how signals used for controlling the system to vary the scanning parameter(s) in scanning frames are input to the components that are positioned inside the patient's body (e.g., on an endoscope). In order to provide integrated imaging and other functionality, system 150 is thus divided into the components that remain external to the patient's body, and those which are used internally (i.e., the components within a dash line 152). A block 154 lists the functional components disposed at the distal end of the scanning optical fiber system. As indicated therein, these exemplary components can include illumination optics, one or more electromechanical scan actuator(s), one or more scanner control actuator(s), one or more scanner motion detector(s) for control of the scanner motion, photon detectors for imaging the ROI, and optionally, additional photon detectors for diagnostic purposes and for therapy and monitoring purposes—one or more of which can be implemented using the same scanning device by varying the parameters of the scanning that are employed during different scanning frames. It should be noted that in regard to system 150, only the functional components actually required for a specific application may be included. Also, the additional functions besides imaging can be diagnostic, or therapy, or a combination of these functions.

Externally, the illumination optics and scanner(s) are supplied light from imaging sources and modulators as shown in a block 156. Further details concerning several preferred embodiments of external light source systems 158 for producing RGB, UV, IR, and high-intensity light conveyed to the distal end of an optical fiber system are either disclosed below or will be evident to a person of ordinary skill in this art. Scanner sensors can be used for controlling the scanning and produce a signal that is fed back to the scanner actuators, illumination source, and modulators to implement the scanning control after signal processing in a block 168.

In block 160, image signal filtering, buffering, scan conversion, amplification, and other processing functions are implemented using the electronic signals produced by the imaging photon detectors and for the other photon detectors employed for diagnosis/therapy, and monitoring purposes. Blocks 156 and 160 are interconnected bi-directionally to convey signals that facilitate the functions performed by each respective block. Similarly, each of these blocks is bi-directionally coupled in communication with a block 162 in which analog-to-digital (A/D) and digital-to-analog (D/A) converters are provided for processing signals that are supplied to a computer workstation user interface or other computing device employed for image acquisition, processing, for executing related programs, and for other functions. Control signals from the computer workstation are fed back to block 162 and converted into analog signals, where appropriate, for controlling or actuating each of the functions provided in blocks 156, 158, and 160. The A/D converters and D/A converters within block 162 are also coupled bi-directionally to a block 164 in which data storage is provided, and to a block 166. Block 166 represents a user interface for maneuvering, positioning, and stabilizing the end of the scanning optical fiber within a patient's body.

In block 164, the data storage is used for storing the image data produced by the detectors within a patient's body, and for storing other data related to the imaging and functions implemented by the scanning optical fiber. Block 164 is also coupled bi-directionally to the computer workstation 168 and to interactive display monitor(s) in a block 170. Block 170 receives an input from block 160, enabling images of the ROI to be displayed interactively. In addition, one or more passive video display monitors may be included within the system, as indicated in a block 172. Other types of display devices 174, for example, a head-mounted display (HMD) system, can also be provided, enabling medical personnel to view an ROI as a pseudo-stereo image.

Dual-Cladding Optical Fiber

Details of an exemplary dual-cladding optical fiber 250 are illustrated in FIG. 3A, which shows a longitudinal cross-sectional view. As shown therein, dual-cladding optical fiber 250 includes a relatively small diameter core 252. Surrounding core 252 is an inner cladding 254, which is substantially larger in diameter than the core. An outer cladding 256 surrounds the inner cladding and has an internally reflective surface that helps to retain and convey light longitudinally within the dual-cladding optical fiber. Typically, for solid-core fused-silica fibers, the core material has a higher refractive index than the surrounding inner cladding, and the outer cladding has a lower refractive index than the inner cladding. The present concept employs a dual-cladding optical fiber to both convey visible light within core 252 while imaging a site, and convey substantially higher power light, e.g., IR light, within inner cladding 254, when rendering therapy to the site. The substantially larger diameter of the inner cladding enables it to readily convey a much higher optical power without material damage, than would be possible in a small diameter singlemode optical fiber. As a result, the dual-cladding optical fiber can be employed with endoscopes that are sufficiently small in diameter to be readily advanced through small diameter lumens within a patient's body. Once advanced to a desired treatment site, the dual-cladding optical fiber can be employed to convey light used for imaging the site, to select a particular region where optical therapy is to be delivered, convey the high-intensity light needed for therapy to the selected region, and then monitor the status of the region after therapy has been provided. Medical personnel can thus readily determine where further therapy may be required and evaluate the status of the region that has already received the therapy.

Triple-Cladding and Other Non-Standard Optical Fibers

Figure 3B:
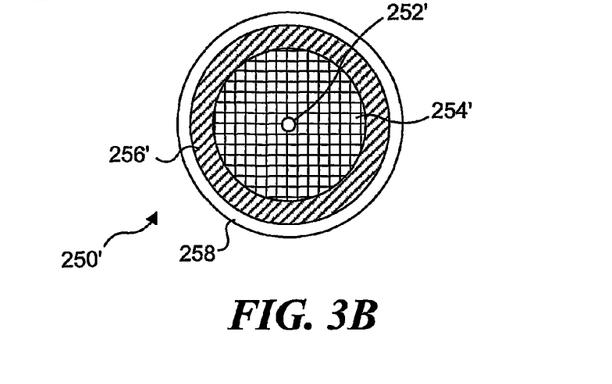
FIG. 3B is a transverse cross-sectional view of a triple-cladding optical fiber suitable for optional use in connection with the approach disclosed below.

An additional outer cladding layer 258 is shown on an exemplary multi-cladding (in this example, a triple-cladding) optical fiber 250' in FIG. 3B. As illustrated in this Figure, triple-cladding optical fiber 250' includes a similar smaller diameter core 252' and inner cladding region 254', just as does dual-cladding optical fiber 250. Surrounding the inner cladding is a first outer cladding 256', followed by additional outer cladding 258. This additional outer cladding serves as a protective coating to the inner dual-cladding optical fiber. The triple-cladding optical fiber provides higher performance by reducing light leakage from the inner dual-cladding fiber, while increasing both the optical and mechanical damage thresholds. While all of the examples discussed below use dual-cladding optical fibers for combined optical imaging and optical therapy, it will be understood that other multi-cladding optical fibers having microstructured, photonic bandgap, and photonic crystal light guiding properties can be employed instead of the dual-clad, solid-core fused-silica optical fiber. It is therefore intended that the solid-core fused-silica material discussed below be viewed as representative of only one type of multi-cladding optical fiber that can be employed in any of the following exemplary embodiments. As indicated by the example shown in FIG. 3B, these multi-cladding optical fibers can have more than two cladding layers.

Coupling Both Visible and High-intensity Light into Dual-Cladding Optical Fiber

Figure 4:
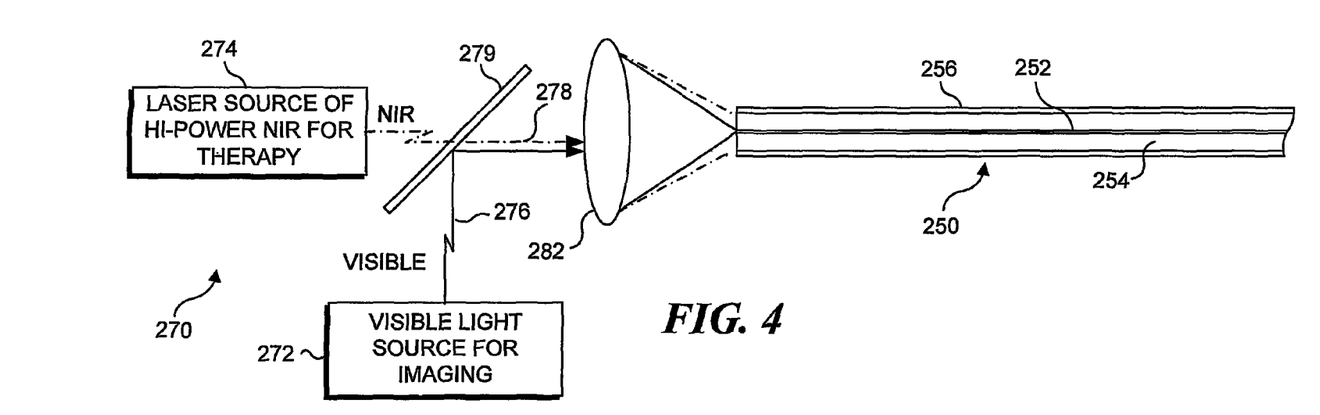
FIG. 4 is a schematic block diagram of a first exemplary embodiment for coupling visible light into a core of a dual-cladding optical fiber and high-power light into an inner cladding of a dual-cladding optical fiber.

Several different exemplary embodiments have been developed for coupling visible light used for imaging into the small diameter core of a dual-cladding optical fiber, and substantially higher power light used for therapy into the inner cladding of the dual-cladding optical fiber. For example, FIG. 4 illustrates an embodiment 270 in which a visible light source for imaging 272 emits visible light 276, while a laser source of high-power near infrared light (NIR) for therapy 274 emits NIR light 278. All of the examples discussed below refer to NIR light for use in rendering therapy, but it will be understood that other wavebands of light of sufficient intensity to provide a therapeutic effect can be employed instead of the NIR light. It is therefore intended that the NIR light be viewed as representative of only one type of high-power light that can be employed in any of the following exemplary embodiments. The references to NIR light in the discussion of the following exemplary embodiment is thus NOT intended to in any way be limiting on the type of high-power light that can be employed in the novel approach that uses dual-cladding optical fibers as described herein.

Both the laser source of high-power NIR light for therapy and the visible light source for imaging are disposed externally of a patient, adjacent to a proximal end of dual-cladding optical fiber 250. Visible light 276 and NIR light 278 are combined into a single beam of light by using a dichroic beamsplitter 279 positioned at a 45-degree angle (e.g., the visible light is reflected by the beamsplitter, while the NIR light is transmitted through it). In one case, the two beams are collimated before being combined and then directed to a lens 282. The lens has chromatic aberration such that the visible wavelength light has a shorter focal length than the NIR light. As a result, visible light 276 is directed by the lens into core 252 of dual-cladding optical fiber 250, while NIR light 278 is directed by the lens into inner cladding 254 of the dual-cladding optical fiber. In a second case (not shown) the visible light is provided as a slightly converging beam, while the NIR light is provided as a slightly diverging beam, before being combined. The different degrees of collimation of the visible and NIR light result in different focal points from lens 282, with the visible light focusing nearer and the NIR light focusing farther from lens 282. In a third case (also not shown), the visible light is directed toward the center of lens 282, while the NIR light is directed to a radially outer portion of the lens. Due to first order optical aberration, such as spherical aberration, the focal points of the two beams of light are spatially displaced, so that the NIR light is focused into the inner cladding, while the visible light is focused into the core of the dual-cladding optical fiber.

Figure 5:
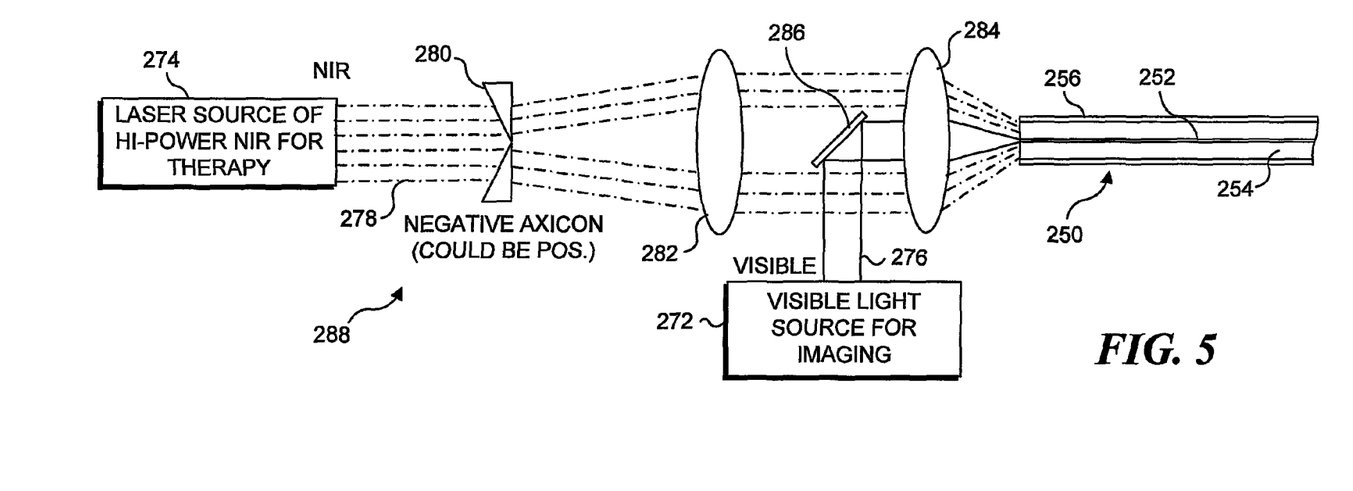
FIG. 5 is a schematic block diagram of a second exemplary embodiment for coupling visible light into a core of a dual-cladding optical fiber and high-power light into an inner cladding of a dual-cladding optical fiber.

An exemplary embodiment 288 for coupling the high-power NIR light and visible light into a dual-cladding optical fiber is illustrated in FIG. 5. In this embodiment, laser source of high-power NIR for therapy 274 again produces NIR light 278 that is collimated and is incident on an axicon 280 and is directed thereby toward lens 282. Alternatively, a positive axicon can be used for this purpose instead of negative axicon 280. Lens 282 collimates and directs the NIR light toward a lens 284, which focuses the NIR light into inner cladding 254. Visible light source for imaging 272 produces visible light 276, which is directed toward a dichroic beam splitter (or 45-degree mirror) 286. The red, green, and blue components of visible light 276 are reflected by the dichroic beam splitter or mirror into lens 284, which focuses the visible light into core 252 of the dual-cladding optical fiber.

Figure 6:
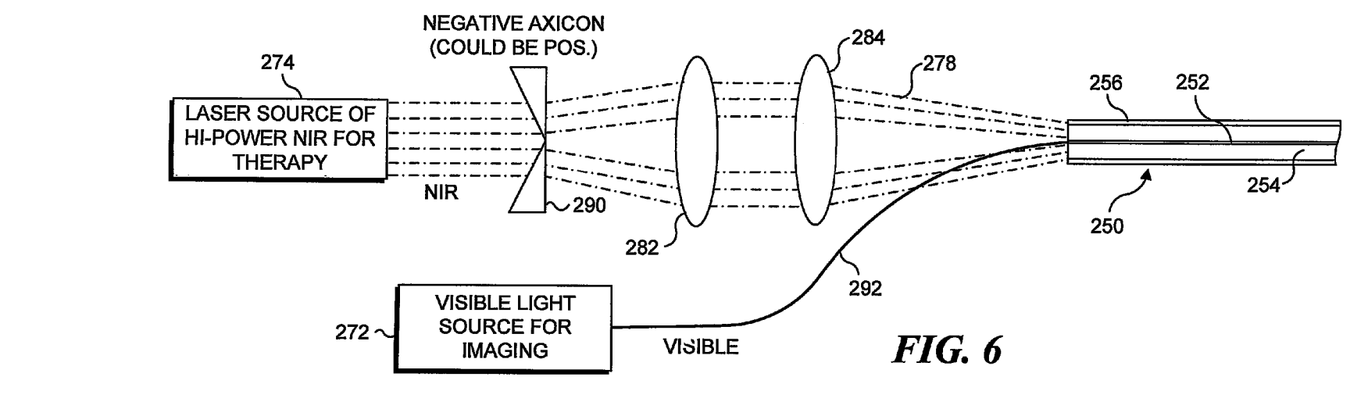
FIG. 6 is a schematic block diagram of a third exemplary embodiment for coupling visible light into a core of a dual-cladding optical fiber and high-power light into an inner cladding of a dual-cladding optical fiber.
Figure 7:
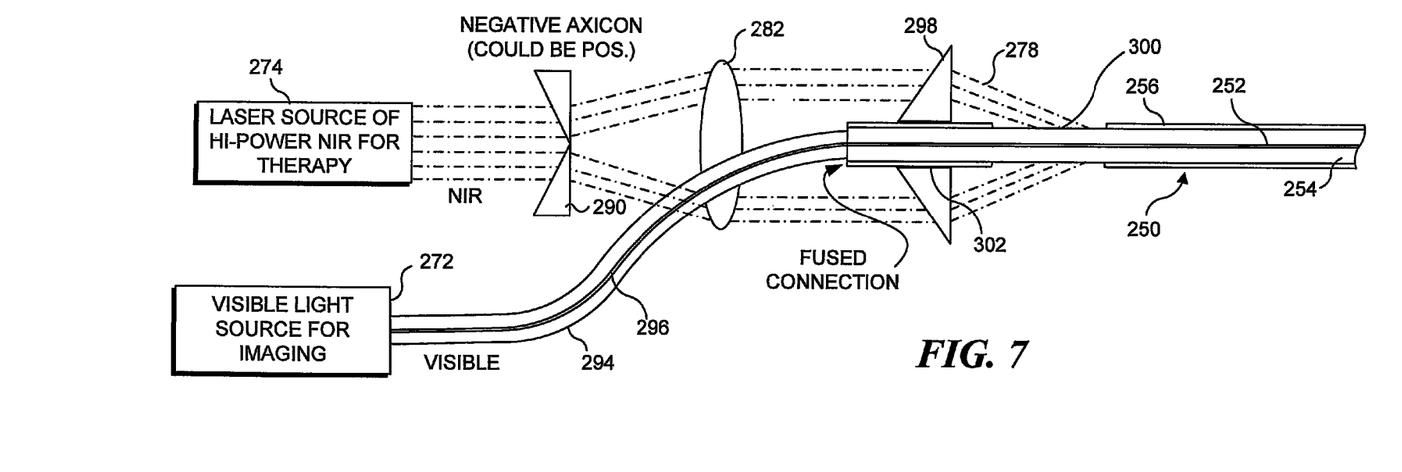
FIG. 7 is a schematic block diagram of a fourth exemplary embodiment for coupling visible light into a core of a dual-cladding optical fiber and high-power light into an inner cladding of a dual-cladding optical fiber.

FIGS. 6 and 7 illustrate two more embodiments for coupling the high-power NIR light and visible light into the dual-cladding optical fiber. In FIG. 6, laser source of high-power NIR for therapy 274 directs the NIR light that it produces through a pair of negative axicons 290, which cause the NIR light to diverge so that the NIR light is directed towards radially outer portions of lens 282. Alternatively, a pair of positive axicons (not shown) could be used instead of negative axicons 290. The NIR light is collimated and directed by lens 282 toward lens 284, which focuses the NIR light along paths 278 into inner cladding 254 of dual-cladding optical fiber 250. Visible light source for imaging 272 produces visible light that is conveyed through a singlemode optical fiber 292, a distal end of which is coupled directly to core 252 at the proximal end of the dual-cladding optical fiber. Singlemode optical fiber 292 has approximately the same diameter as core 252, and is readily coupled to core 252, for example, by fusing. Typically, singlemode single-cladding and singlemode dual-cladding optical fibers have the same outer diameter, so after fusing the singlemode optical fiber to the dual clad optical fiber, the outer region of the cladding of the singlemode optical fiber scan be etched down to approximately 10 microns diameter using hydrofluoric (HF) acid and optically smooth surfaces can be formed using $CO_2$-laser annealing. Furthermore, the relatively small diameter of singlemode optical fiber 292 does not significantly block or scatter the NIR light traveling along paths 278 toward inner cladding 254 of the dual-cladding optical fiber.

In FIG. 7, the NIR light from axicon 290 is again directed to lens 282, which collimates the NIR light and directs it toward an axicon 298. Axicon 298 has a central orifice 302 through which the proximal end of dual-cladding optical fiber 250 extends. The collimated NIR light is directed by axicon 298 along paths 278 toward a gap 300 formed where outer cladding 256 of dual-cladding optical fiber 250 has been etched away and the exposed outer surface of inner cladding 254 has been polished. The NIR light enters into inner cladding 254 at gap 300 and is conveyed toward the distal end of the dual-cladding optical fiber. Visible light from visible light source for imaging 272 is conveyed through a singlemode optical fiber 294 within a core 296. Singlemode optical fiber 294 is fused to the proximal end of dual-cladding optical fiber 250, and core 296 conveys the visible light correctly into core 252 of the dual-cladding optical fiber.

As a variation (not shown), axicon 298 can be replaced with a regular prism that is fused to one side of dual-cladding optical fiber 250 in place of axicon 298, proximal of gap 300, so that NIR light from lens 282 is similarly directed by the prism into inner cladding 254, which is exposed at gap 300. It should also be understood that the diameter of singlemode optical fiber 294 could be substantially reduced (compared to what is shown in FIG. 7, to decrease scattering of the NIR light, and a reflective coating can be applied to the outer surface of the singlemode optical fiber to prevent NIR light from entering core 296 and to prevent damage to the optical fiber.

Figure 8:
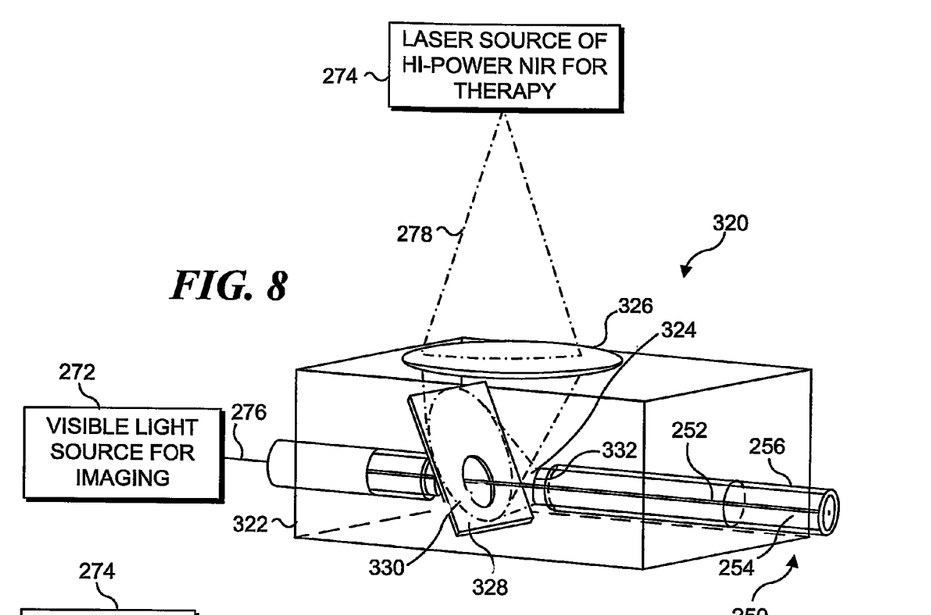
FIG. 8 is a schematic block diagram of a fifth exemplary embodiment for coupling visible light into a core of a dual-cladding optical fiber and high-power light into an inner cladding of a dual-cladding optical fiber.

FIG. 8 illustrates an embodiment 320 that employs a matrix 322 having an index of refraction substantially matching that of inner cladding 254 in dual-cladding optical fiber 250. In this embodiment, both outer cladding 256 and inner cladding 254 are etched away, exposing core 252 and forming a gap 324 adjacent to the proximal end of the dual-cladding optical fiber. Matrix 322 surrounds core 252 where it is thus exposed. Visible light 276 emitted by visible light source for imaging 272 is conveyed into core 252 at the proximal end of the dual-cladding optical fiber. NIR light 278 is emitted by the laser source of high-power NIR for therapy with a numerical aperture (NA) that forms a laser light cone. The laser light cone is directed toward a convex lens 326, which focuses the NIR light into matrix 322 and on to an angled mirror 328. The reflective surface of mirror 328 reflects the NIR light into an exposed end 332 of inner cladding 254. Mirror 328 includes an orifice 330 having a diameter sufficiently large to enable the proximal end of dual-cladding optical fiber 250 pass through the orifice after core 252 is exposed within gap 324. The assembly comprising mirror 328 and dual-cladding optical fiber 250 can then be fixed in matrix 322, for example, by potting the matrix around the assembly.

Figure 9A:
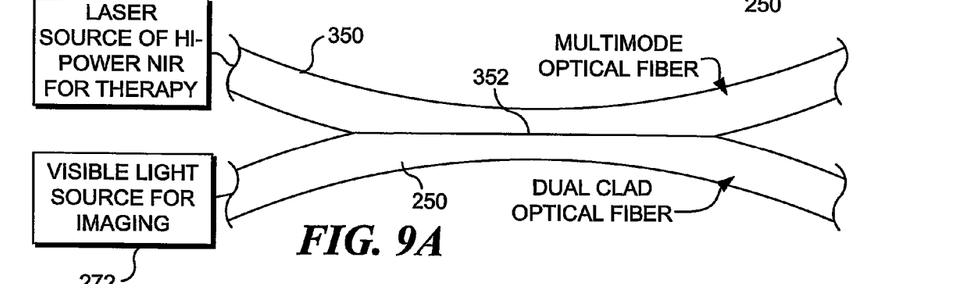
FIGS. 9A and 9B respectively illustrate sections of a dual-cladding optical fiber and a multimode optical fiber that are coupled together so that relatively high-intensity light being conveyed through the multimode optical fiber is introduced into the inner cladding of a dual-cladding optical fiber that is able to carry visible light within its core, and a cross-section of the two optical fibers.

Yet another technique for coupling NIR light into inner cladding 254 employs coupling between optical fibers to add high-power NIR for therapy into the inner cladding of a dual-cladding optical fiber. FIG. 9A illustrates how two optical fibers are coupled together so that NIR light from the laser source of high-power NIR for therapy is conveyed from the core of an optical fiber 350 and into the inner cladding of dual-cladding optical fiber 250. Visible light from the visible light source is directly conveyed into the core of dual-cladding optical fiber 250. Not shown in this Figure is a mounting holder, which as discussed below, retains the two optical fibers in a light coupling relationship.

In this embodiment, optical fiber 350 is a multimode optical fiber having a core 354 with the same dimensions and optical properties as the inner cladding of dual-cladding optical fiber 250. These two optical fibers are coupled together along a coupling section 352. The high-intensity light being conveyed through the core of the multimode optical fiber is thus coupled into the inner cladding of the dual-cladding optical fiber where the two are in contact with each other at coupling section 352.

Figure 9B:
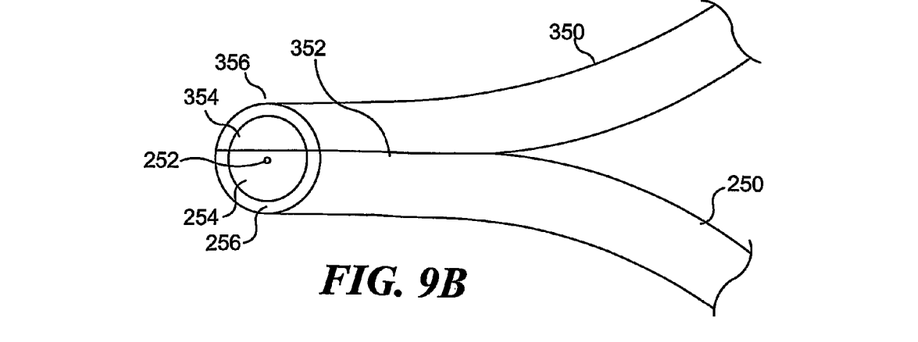
Figure 9C:
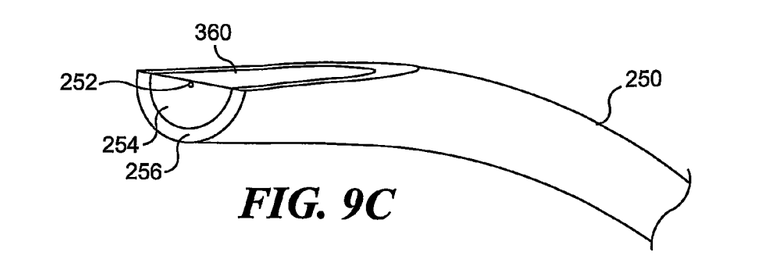
FIG. 9C illustrates an end view of the dual-cladding optical fiber, showing the polished section that is intended to couple with the multimode optical fiber of FIGS. 9A and 9B.

Further details of coupling section 352 are illustrated in the cross-section shown in FIG. 9B. Dual-cladding optical fiber 250 includes a flattened section 360 where the optical fiber is polished through outer cladding and part way through the inner cladding, as shown in the cross-sectional view of FIG. 9C. Similarly, multimode optical fiber 350 is also polished through a cladding 356 and part way into core 354 to form a corresponding flattened section (not shown). Both of these flattened sections are then polished, as explained below.

Figure 10:
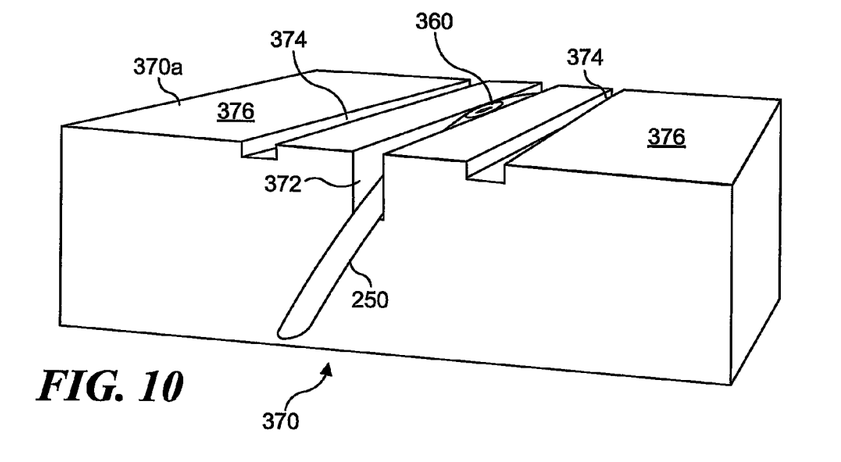
FIG. 10 illustrates a bottom portion of a fixture that is intended to couple together polished sections of a dual-cladding optical fiber and a multimode optical fiber to achieve the configuration shown in FIGS. 9A and 9B.
Figure 11:
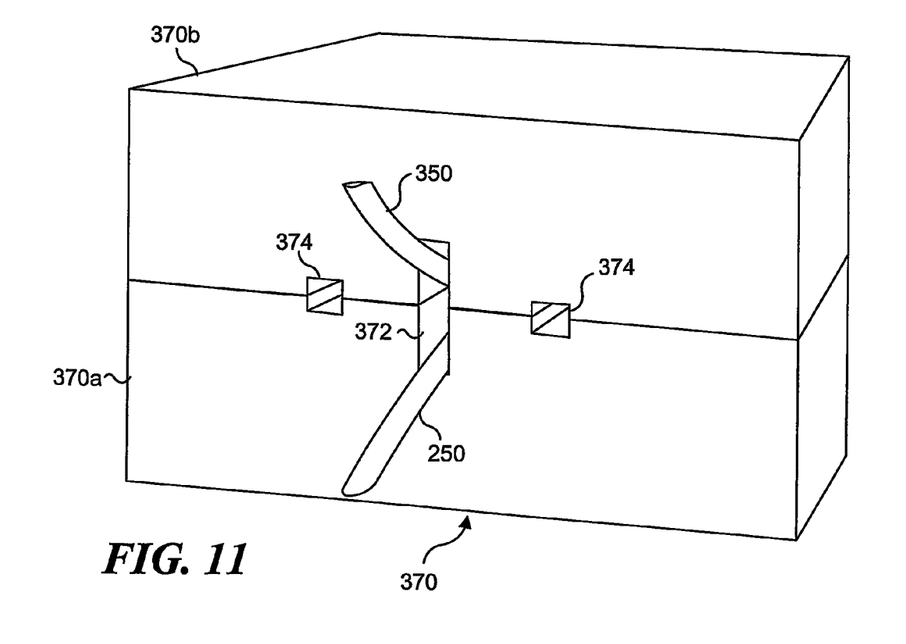
FIG. 11 illustrates the complete fixture, showing how portions of the dual-cladding optical fiber and multimode optical fiber are held together in light coupled relationship.

FIGS. 10 and 11 illustrate how dual-cladding optical fiber 250 and multimode optical fiber 350 are held together in a coupled relationship, using a mounting holder 370 comprising a lower block 370a and an upper block 370b. FIG. 10 illustrates lower block 370a with dual-cladding optical fiber 250 disposed in a central groove 372 shaped so as to force the dual-cladding optical fiber to form an arc, with flattened section 360 disposed at the top of the arc. Upper block 370b is identical to lower block 370a. Flattened section 360 of dual-cladding optical fiber 250 is polished to have the same thickness as the depth of groove 372 at the top of the arc. Similarly, multimode optical fiber 350 is disposed in groove 372 of upper block 370b and is polished so that its thickness at the center of the arc of multimode optical fiber 350 is equal to the depth of groove 372 at that point. The polishing of flattened section 360 in dual-cladding optical fiber 250 is carefully done so as to just miss core 252.

The polished flattened portions of the dual-clad and multimode optical fibers are then brought into contact, aligned, and fixed in place with mounting holder 370. An adhesive is applied to the facing surfaces or bonding pads 376 of the upper block and the lower block, which are thus held together, forming mounting holder 370, as shown in FIG. 11. Adhesive stop grooves 374 are formed in the facing surfaces of lower block 370a and upper block 370b, parallel to and spaced apart from each side of groove 372. Adhesive stop grooves 374 prevent adhesive from wicking into coupling section 352 where dual-cladding optical fiber 250 contacts multimode optical fiber 350. The coupling ratio from one optical fiber to the other is determined by the radius of curvature of the dual-clad and multimode optical fibers as they bend to form their respective diverging arcs within groove 372.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. Apparatus for imaging a site within a patient's body and rendering therapy to a desired region of the site, comprising:
    (a) a multi-cladding optical fiber that includes a core having a core diameter, an inner cladding having an inner cladding diameter, and an outer cladding, all extending generally between a proximal end and a distal end of the multi-cladding optical fiber;
    (b) an imaging light source that produces an imaging light for use in illuminating the site within the patient's body to produce an image of the site, the imaging light being directed into the core of the multi-cladding optical fiber at the proximal end and being conveyed to the distal end of the multi-cladding optical fiber, for emission toward the site to be imaged;
    (c) a therapy light source that produces therapy light having a substantially greater optical power than the imaging light, the therapy light being directed into the inner cladding at the proximal end and being conveyed to the distal end of the multi-cladding optical fiber, to render therapy to the desired region of the site, the inner cladding diameter substantially greater than the core diameter to convey the therapy light the having substantially greater optical power than the imaging light and wherein the inner cladding having the diameter substantially larger than the core diameter is capable of transmitting substantially greater optical power of the therapy light than the core is capable of transmitting without material damage;
    (d) an actuator disposed adjacent to the distal end of the multi-cladding optical fiber, the actuator being selectively energized so as to move the distal end of the core and the inner cladding in a desired path, both while imaging the site using the imaging light to illuminate and while rendering therapy to the desired region of the site with the therapy light emitted from the inner cladding and directed toward the desired region; and
    (e) at least one sensor for receiving light from the site that is being imaged, the at least one sensor producing a signal useful for producing an image of the site in response to the light received therefrom as a result of the imaging light illuminating the site.

2. The apparatus of claim 1, further comprising a housing disposed at the distal end of the multi-cladding optical fiber, the housing supporting a lens system for focusing the imaging light and the therapy light emitted from the distal end of the multi-cladding optical fiber onto the site.

3. The apparatus of claim 2, wherein the at least one sensor is disposed adjacent to the distal end of the multi-cladding optical fiber and supported by the housing to receive light, the signal produced by the at least one sensor being conveyed through at least one electrical lead that extends generally to the proximal end of the multi-cladding optical fiber.

4. The apparatus of claim 1, further comprising at least one additional optical fiber for conveying light received from the site toward the proximal end of the multi-cladding optical fiber, wherein the at least one sensor is disposed adjacent to the proximal end of the multi-cladding optical fiber and is coupled to the at least one additional optical fiber.

5. The apparatus of claim 1, further comprising an axicon for coupling the therapy light from the therapy light source into the inner cladding of the multi-cladding optical fiber, enabling the imaging light from the imaging light source to be directed into the core of the multi-cladding optical fiber, at the proximal end thereof.

6. The apparatus of claim 5, further comprising a proximal lens system for focusing at least one of the therapy light into the inner cladding, and the imaging light into the core.

7. The apparatus of claim 6, wherein the proximal lens system includes a reflective surface that reflects at least one of the therapy light into the inner cladding or the imaging light into the core.

8. The apparatus of claim 6, wherein an outer cladding is removed from a segment of the multi-cladding optical fiber adjacent to the proximal end, exposing the inner cladding within the segment, and wherein the lens system directs the therapy light into the inner cladding at the segment, so that the therapy light is conveyed through the inner cladding toward the distal end of the multi-cladding optical fiber.

9. The apparatus of claim 1, further comprising a multimode optical fiber that is coupled to the therapy light source to receive the therapy light, an outer cladding being removed from the multimode optical fiber along a segment thereof, exposing a multimode core that conveys the therapy light, the multimode core that is exposed being polished, wherein an outer cladding is also removed from a segment of the multi-cladding optical fiber, exposing the inner cladding, the inner cladding at the segment also being polished and affixed in contact with the multimode core that is polished to facilitate transfer of the therapy light from the multimode core into the inner cladding, so that the therapy light can be conveyed through the inner cladding toward the distal end of the multi-cladding optical fiber.

10. The apparatus of claim 9, further comprising a fixture to support the multimode core that is polished in a light coupling relationship with the inner cladding that is polished.

11. The apparatus of claim 1, further comprising a proximal lens system that includes a reflective surface, wherein the outer cladding and the inner cladding are removed from a segment of the multi-cladding optical fiber adjacent to the proximal end, forming a gap around the core in which the reflective surface is disposed, the proximal lens system focusing the therapy light toward the reflective surface so that the therapy light is reflected therefrom and into an end of the inner cladding comprising one side of the gap, the therapy light thus being directed toward the distal end of the multi-cladding optical fiber within the inner cladding.

12. The apparatus of claim 1, wherein the treatment light comprises one or more of infrared light, near infrared light or visible light.

13. The apparatus of claim 1, wherein the imaging light comprises one or more visible light, red light, green light or blue light.

14. The apparatus of claim 1, wherein the core comprises a single mode core.

15. The apparatus of claim 1, wherein the therapy light source provides an optical power greater than 100 mW.

\* \* \* \* \*